(12) United States Patent
Hawe

(10) Patent No.: US 6,807,843 B1
(45) Date of Patent: Oct. 26, 2004

(54) GAS SENSOR

(75) Inventor: David Lee Hawe, Villa Park, CA (US)

(73) Assignee: C-Squared, Inc., Anaheim, CA (US)

( * ) Notice: Subject to any disclaimer, the term of this patent is extended or adjusted under 35 U.S.C. 154(b) by 0 days.

(21) Appl. No.: 10/684,279

(22) Filed: Oct. 11, 2003

(51) Int. Cl.[7] ............ G01R 27/08; G01N 9/00; G01N 7/00

(52) U.S. Cl. ............ 73/23.2; 73/31.05; 324/693; 324/706

(58) Field of Search ............... 73/23.2, 31.05, 73/23.41, 23.3, 23.31, 23.21; 423/82, 84, 83, 94, 96; 324/693, 706

(56) References Cited

U.S. PATENT DOCUMENTS 6,548,024 B1 * 4/2003 Doncaster et al. ............ 422/88

* cited by examiner

Primary Examiner—Hezron Williams
Assistant Examiner—Tamiko Bellamy
(74) Attorney, Agent, or Firm—Dennis W. Beech

(57) ABSTRACT

The gas sensor may be an apparatus for sensing a proportion of a gas in a gas mixture. A gas sensor may have a sampling element slidably engaged with a sensor element. The sensor element may have a sensing chamber therein with an inlet passage and an outlet passage formed in the sensor element wherein the inlet passage and the outlet passage may be in communication with the sensing chamber and externally to the sensor element. A first detector may be positioned in the sensing chamber with a first pair of external contacts passing through the sensor element terminating externally thereto. The sensor element may have a reference chamber therein with a second detector positioned therein and a second pair of external contacts passing through the sensor element terminating externally thereto. The sampling element may have a sample chamber therein with the sensor element forming a portion of the sample chamber. There may be a gas inlet port in the sampling element that may be in communication with the sample chamber and externally to the sample element.

9 Claims, 1 Drawing Sheet

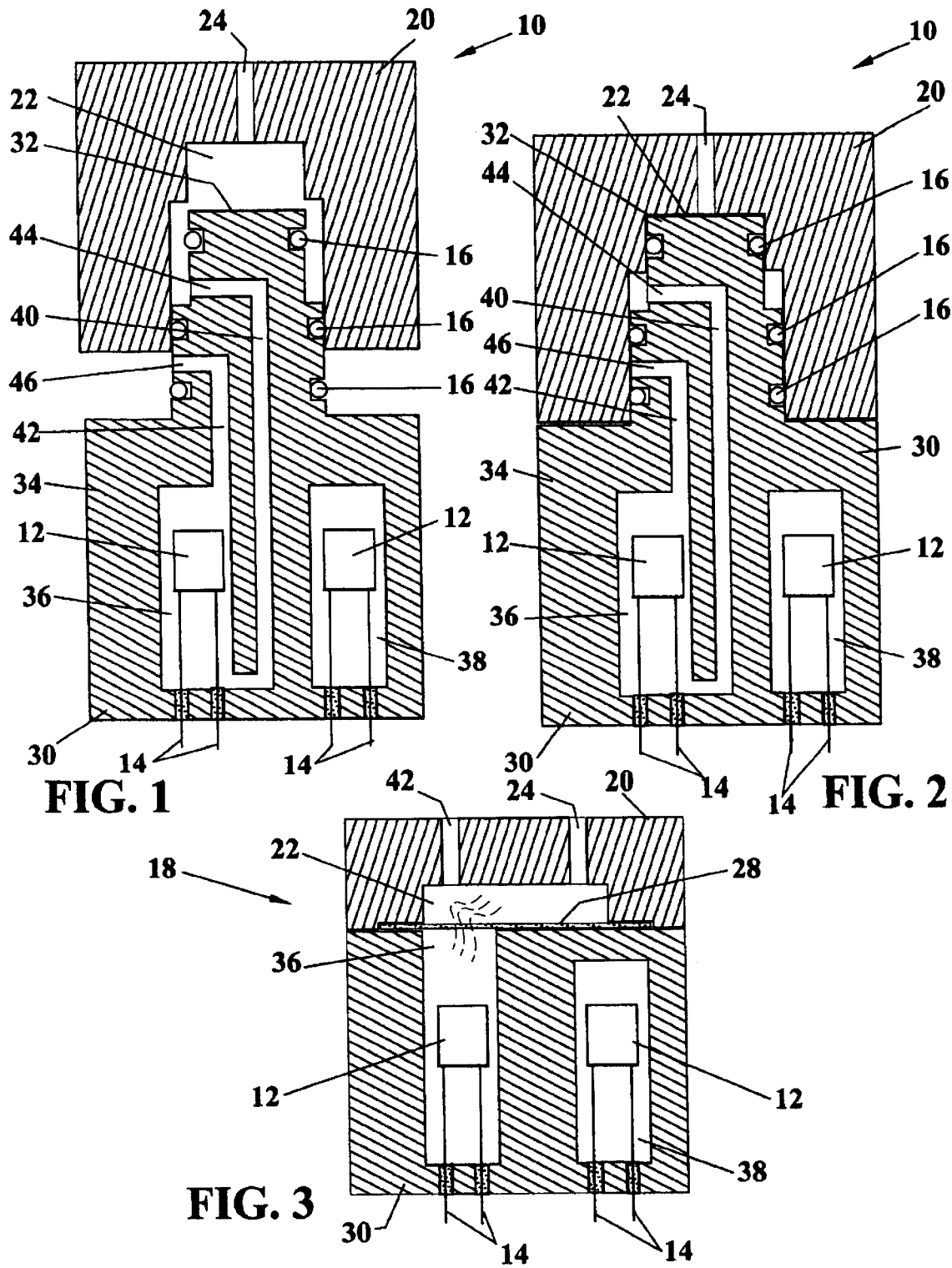

GAS SENSOR

BACKGROUND OF THE INVENTION

This invention relates to devices for sensing the relative proportion of a gas in a mixture of gasses. The new gas sensor device may compare a known gas or gas mixture to a varying or fluctuating gas mixture for use in measuring the amount of a particular gas in the varying mixture.

Devices currently exist for use in sensing the amount of a gas in a continuously flowing gas mixture. As an example, for underwater human divers it may be important to know the amount of helium in a breathing mixture being supplied to the diver from gas tanks. A device that includes a temperature sensitive coil of wire suspended in a chamber therein may be used to detect changes in the thermal conductivity of a gas mixture flowing through the chamber if the gas composition changes.

A detector wire coil in the gas flow through chamber may be compared to a reference wire coil in a separate chamber containing a gas mixture of a chosen mixture content. The electric current difference between the two wire coils may be measured as for example by use of a Wheatstone bridge. The percent variation based on the varying conductivity with temperature of the wire coil may be used to calculate the amount of helium in the gas flow mixture. This type of device may also be used to detect other gas percentages as well. For example, hydrogen content may be similarly measured when mixed with nitrogen, oxygen or air.

The difficulty in using such devices in an underwater diving environment or other limited control measuring environment may be the need to provide a relative uniform gas mixture flow rate through the detector wire coil chamber for comparison to the reference wire coil. To the extent this is not well controlled the temperature change at the detector wire coil may not be principally due to the helium, hydrogen or other gas mixture changes and therefore the comparison measurement may be inaccurate. Also the suspension of the wire coil in the chamber may cause problems due to the vulnerability of the wire to the gas flow environment and other factors such as impact to the device.

SUMMARY OF THE INVENTION

The present invention is directed to apparatus for sensing a proportion of a gas in a gas mixture. A gas sensor may have a sampling element slidably engaged with a sensor element. The sensor element may have a sensing chamber therein with an inlet passage and an outlet passage formed in the sensor element wherein the inlet passage and the outlet passage may be in communication with the sensing chamber and externally to the sensor element. A first detector may be positioned in the sensing chamber with a first pair of external contacts passing through the sensor element terminating externally thereto. The sensor element may have a reference chamber therein with a second detector positioned therein and a second pair of external contacts passing through the sensor element terminating externally thereto. The sampling element may have a sample chamber therein with the sensor element forming a portion of the sample chamber. There may be a gas inlet port in the sampling element that may be in communication with the sample chamber and externally to the sample element.

These and other features, aspects and advantages of the present invention will become better understood with reference to the following drawings, description and claims.

BRIEF DESCRIPTION OF THE DRAWINGS

FIG. 1 illustrates a side cross sectional view of a gas sensor according to an embodiment of the invention;

FIG. 2 illustrates a side cross sectional view of a gas sensor in a closed position according to an embodiment of the invention;

FIG. 3 illustrates a side cross sectional view of an alternate gas sensor according to an embodiment of the invention.

DETAILED DESCRIPTION

The following detailed description represents the best currently contemplated modes for carrying out the invention. The description is not to be taken in a limiting sense, but is made merely for the purpose of illustrating the general principles of the invention.

Referring to FIGS. 1 and 2, a gas sensor 10 may have a sampling element 20 slidably engaged with a sensor element 30 wherein the sensor element 30 may have an upper portion 32 sized to be insertable in a sample chamber 22 of the sample element 20. There may be a gas inlet port 24 in the sampling element 20 for flow of gas from the environment into the sample chamber 22. The sampling element 20 may be of any suitable form such as cylindrical similar to a cap enclosure or rectangular, etc. The sensor element 30 may also be cylindrical or other suitable shape having compatibility between the two elements The sensor element 30 may have upper portion 32 and lower portion 34 that may have outer dimensions that are generally similarly proportioned or not. For example, the upper portion 32 and lower portion 34 may have the same exterior form factor and the entire sensor element 30 may slide into the sampling element 20 or partially slide into the sampling element 20. For purposes of the disclosure only, the upper portion 32 may be illustrated as having a narrower upper portion 32 compared to the lower portion 34. The upper portion 32 exterior may be shaped to closely align with the interior walls of the sample chamber 22 when slideably inserted therein.

The sensor element 30 may have a sensing chamber 36 and a reference chamber 38 formed therein with each isolated from the other. Each chamber 36, 38 may have a thin film thermal conductivity detector 12 or platinum thin film resistive element disposed therein with external contacts 14 extending through the walls of the chambers 36, 38. The external contacts 14 may be connected to an electronic measuring device, such as, a Wheatstone bridge for measuring current or other circuit parameter measurements, to detect change in the conductivity of the detectors 12. The reference chamber 38 may have a known gas or mixture contained therein to establish a reference temperature for the detector 12 disposed in the reference chamber 38.

The sensor element 30 may have an inlet passage 40 and an outlet passage 42 between sensing chamber 36 and the exterior of the sensor element 30. The inlet passage 40 may be positioned to receive gas from the sample chamber 22 when the sensor element 30 is partially inserted in the sampling element 20 as illustrated in FIG. 1. The inlet passage 40 may have inlet open end 44 positioned in sample chamber 22 to allow gas to flow from the sample chamber 22 to sensing chamber 36. The gas flow may then exit the sensing chamber 36 through outlet passage 42 when the gas sensor 10 is in the open position as illustrated in FIG. 1.

When it may be desired to measure the amount of a particular gas such as helium in a gas mixture, the gas sensor 10 may be moved to the closed position as illustrated in FIG. 2. In this position the inlet passage 40 may not be able to receive gas exposed to gas inlet port 24 and the outlet open end 46 may be closed by the interior wall of sample chamber 22. Also, gas in sensing chamber 36 and passages 40, 42 may not be able to exit the sensor element 30. In the steady state condition created in the closed position the thermal conductivity difference between the gas in the reference chamber 38 and the sensing chamber 36 may be determined with knowledge of the temperature difference of the detectors 12 based on exposure to various gasses or gas mixtures, for example, a percentage of helium in a mixture in the sensing chamber 36 may be determined. In the case of underwater divers, this may be very important to their survival.

Several O-rings 16 may be used to seal the elements of the sample chamber 22 to inhibit flow of gas out of the sample chamber 22 other than into inlet passage 40 or for gas to flow in or out of the sensing chamber 36 when the gas sensor 10 may be in the closed position.

Referring to FIG. 3, a continuous flow gas sensor 18 may have a sampling element 20 with a gas inlet port 24 and an outlet passage 42 in fluid communication with a sample chamber 22. The sample chamber 22 may have a gas porous permeable membrane 28 as the interface for a gas or gas mixture to diffuse from the sample chamber 22 to sensing chamber 36 in a sensor element 30 for exposure to a detector 12. The continuous flow gas sensor 18 may then be used to measure the proportion of a particular gas in a gas mixture similar to that discussed previously except that there may be no open and closed position prior to electrical measurement. Rather the gas content may be measured as the gas may continue to flow through the continuous flow gas sensor 18.

While the invention has been particularly shown and described with respect to the illustrated embodiments thereof, it will be understood by those skilled in the art that the foregoing and other changes in form and details may be made therein without departing from the spirit and scope of the invention.

I claim:

1. An apparatus for sensing a proportion of a gas in a gas mixture comprising:

a sampling element slidably engaged with a sensor element;

said sensor element having a sensing chamber therein with an inlet passage and an outlet passage formed in said sensor element wherein said inlet passage and said outlet passage in communication with said sensing chamber and externally to said sensor element;

a first detector positioned in said sensing chamber with a first pair of external contacts passing through said sensor element and terminating externally thereto;

said sensor element having a reference chamber therein with a second detector positioned therein and a second pair of external contacts passing through said sensor element terminating externally thereto; and said sampling element having a sample chamber therein with said sensor element forming a portion of said sample chamber, said inlet passage having an inlet open end positioned in said sample chamber, and a gas inlet port in communication with said sample chamber and eternally to said sampling element.

2. The apparatus as in claim 1 wherein:

said inlet passage having an inlet open end positioned to be open to said sample chamber when said sampling element is in an open position and said inlet open end is closed to said sample chamber when said sampling element is in a closed position; and said outlet passage having an outlet open end positioned in the environment when said sampling element is in said open position and said outlet open end is closed to the environment when said sampling element is in said closed position.

3. The apparatus as in claim 1 wherein said first detector and said second detector are formed as a platinum thin film resistive element and said first pair of external contacts and said second pair of external contacts are connected to an electrical conductivity measuring device.

4. The apparatus as in claim 3 wherein said electrical conductivity measuring device is a Wheatstone bridge.

5. The apparatus as in claim 1 wherein said sensor element having an upper portion for slidable insertion in said sample chamber and a lower portion containing said sensing chamber and said reference chamber.

6. The apparatus as in claim 1 wherein an O-ring is used to inhibit flow of gas between said sample chamber internal wall and said sensor element external surface when in slidable engagement.

7. An apparatus for sensing a proportion of a gas in a gas mixture comprising:

a sampling element engaged with a sensor element wherein a gas porous permeable membrane is disposed between said sampling element and said sensor element;

said sensor element having a sensing chamber with an inlet open end;

a first detector positioned in said sensing chamber with a first pair of external contacts passing through said sensor element and terminating externally thereto;

said sensor element having a reference chamber therein with a second detector positioned therein and a second pair of external contacts passing through said sensor element terminating externally thereto; and said sampling element having a sample chamber therein in fluid communication with said sensing chamber through said gas porous permeable membrane, and a gas inlet port and an outlet passage in communication with said sample chamber and eternally to said sampling element.

8. The apparatus as in claim 7 wherein said first detector and said second detector are formed as a platinum thin film resistive element and said first pair of external contacts and said second pair of external contacts are connected to an electrical conductivity measuring device.

9. The apparatus as in claim 8 wherein said electrical conductivity measuring device is a Wheatstone bridge.

* * * * *